United States Patent
Hamachi et al.

(10) Patent No.: US 7,300,648 B2
(45) Date of Patent: Nov. 27, 2007

(54) POLYORGANOSILOXANE EMULSION COMPOSITION AND A COSMETIC MATERIAL MADE THEREFROM

(75) Inventors: Tadashi Hamachi, Chiba (JP); Masaru Ozaki, Chiba (JP); Hidefumi Tanaka, Chiba (JP)

(73) Assignee: Dowecorning Toray Silicone, Co., Ltd., Tokyo (JP)

( * ) Notice: Subject to any disclaimer, the term of this patent is extended or adjusted under 35 U.S.C. 154(b) by 237 days.

(21) Appl. No.: 10/475,377

(22) PCT Filed: Apr. 25, 2002

(86) PCT No.: PCT/JP02/04182

§ 371 (c)(1),
(2), (4) Date: Oct. 21, 2003

(87) PCT Pub. No.: WO02/088253

PCT Pub. Date: Nov. 7, 2002

(65) Prior Publication Data

US 2004/0138373 A1    Jul. 15, 2004

(30) Foreign Application Priority Data

Apr. 27, 2001   (JP) ............................. 2001-130923

(51) Int. Cl.
*A61Q 5/00*   (2006.01)
*C08L 83/04*  (2006.01)

(52) U.S. Cl. .................. 424/70.1; 424/70.12; 424/401; 524/860; 524/863; 524/147; 524/166; 524/210

(58) Field of Classification Search ..................... None
See application file for complete search history.

(56) References Cited

U.S. PATENT DOCUMENTS 4,096,160 A * 6/1978 Ashby .................. 556/459
5,254,333 A * 10/1993 Kajino et al. ............ 424/70.11
5,280,099 A *  1/1994 Imperante et al. ............ 528/28
5,720,964 A *  2/1998 Murray ........................ 424/401
5,776,444 A *  7/1998 Birtwistle et al. ........ 424/70.12
5,990,059 A * 11/1999 Finel et al. .................. 510/122
6,274,130 B1 *  8/2001 Murray .................... 424/70.12
6,319,980 B1 * 11/2001 Ishikawa et al. ............ 524/588
6,432,894 B1 *  8/2002 Maurin et al. ............... 510/122
6,627,698 B2 *  9/2003 Wrolson et al. ............ 524/837
6,737,050 B2 *  5/2004 Doi et al. ................. 424/70.27

FOREIGN PATENT DOCUMENTS

EP    0427210 A2   5/1991
JP    2992366      2/1998
JP    10110161     4/1998

OTHER PUBLICATIONS

English Translation of JP 11-222554, Aug. 1999, Sachiko et al. Obtained from JPO Web-site.*
English language translation of JP2992366 extracted from JPO database.
English language translation JP10110161 extracted from JPO database.

* cited by examiner

*Primary Examiner*—Marc S. Zimmer
(74) *Attorney, Agent, or Firm*—Howard & Howard Attorneys, P.C.

(57) ABSTRACT

A polyorganosiloxane emulsion composition characterized by comprising (A) a polyorganosiloxane, (B) an N-acylalkyl taurine and/or a salt thereof, and (C) water, the content of cyclic organosiloxane oligomers in said component (A) being within 3.5 wt. %, and a cosmetic raw material characterized by consisting of said polyorganosiloxane emulsion composition. The emulsion composition is characterized by superior cosmetic functionality in terms of moisture and smoothness.

21 Claims, No Drawings

POLYORGANOSILOXANE EMULSION COMPOSITION AND A COSMETIC MATERIAL MADE THEREFROM

TECHNICAL FIELD

The present invention relates to a polyorganosiloxane emulsion composition and to a cosmetic raw material obtained from this composition. More specifically, the invention relates to stable polyorganosiloxane emulsion compositions that possess excellent cosmetic functions required for dampness and smoothness, as well as to a cosmetic raw material suitable for the preparation of hair-care and skin-care cosmetics.

BACKGROUND

Japanese Patent Publication (Kokoku) Nos. Sho 34-2041, Sho 41-13995, Sho 43-18800, and Sho 44-20116 describe high-molecular-weight organopolysiloxanes with viscosities varying in a wide range from a silicone oil to a silicone gum that can be obtained by subjecting a low-molecular-weight cyclic organosiloxane to emulsification dispersion, and ring-opening polymerization in the presence of a surface-active agent and a polymerization catalyst.

Normally, the aforementioned low-molecular-weight organosiloxanes required for emulsion polymerization are used in the form of a cyclic organosiloxane oligomer such as octamethylcyclotetrasilane which is readily available and can be easily emulsified and polymerized by ring-opening. However, because ring-opening polymerization of the cyclic organosiloxane oligomer is an equilibrium reaction, upon completion of emulsion polymerization, the polyorganosiloxane normally contains the cyclic organosiloxane oligomers, such as octamethylcyclotetrasiloxane, in an amount of 8 to 15 wt. %. Furthermore, the obtained emulsion system has low physical stability because of the volatile nature of the obtained oligomers. When hair-care cosmetic materials dispersed in aforementioned emulsions are used in large amounts, e.g., in such places as beauty salons, especially when the hair-care product is used for heat-blow treatment of hair, the cyclic organosiloxane oligomer evaporated from the emulsion may contaminate the environment either by polluting the ventilation system, or by damaging contacts of fan heaters or various other electrical appliances.

Furthermore, when the aforementioned emulsion is used in conjunction with skin-care products, volatility of the siloxane oligomer may lead to undesired contact of the oligomer with the skin.

Therefore, when a polyorganosiloxane emulsion is used for preparation of cosmetic products, it may be required to limit the amount of cyclic organosiloxane oligomers used in the emulsion. However, it is difficult to selectively delete only residual cyclic organosiloxane that remains after the emulsion polymerization, without deteriorating the polyorganosiloxane emulsion.

Japanese Patent Publication (Kokoku) No. Sho 41-13995, Japanese Patent Application Publication (Kokai) Nos. Sho 63-265924 and Hei 4-178429 disclose a process, in which a polydiorganosiloxane having molecular ends capped with silanol groups is emulsified in water in the presence of a sulfonic acid catalyst that possesses a surface-active action such as a benzenesulfonic acid substituted with an aliphatic hydrocarbon group, in a high-pressure homogenizer. Upon completion of emulsification, the emulsion is retained at room temperature and is polymerized. A substance, which is normally used in emulsion polymerization as a catalyst that also functions as a surface-active agent, is an easy emulsifiable and readily available dodecylbenzenesulfonic acid, or a similar alkylbenzenesulfonic acid.

However, when an alkylbenzenesulfonic acid is used, even though it is neutralized after polymerization, salts thereof remain in the emulsion, and when the emulsion is in use, these salts change color under the effect of ultraviolet rays.

Furthermore, the use of alkylbenzenesulfonic acids is undesirable from the environmental point of view because of their low biodegradation. alkylbenzenesulfonic acid salts possess high detergency. Therefore, when a polyorganosiloxane emulsion prepared with an alkylbenzenesulfonic acid is used as a raw material for cosmetic products, an excessive amount of these salts irritates skin of the body, skin of the head, and hair. This not only decreases the effect of the cosmetic products, but also may cause irritation of the skin, appearance of dandruff on the head skin, and damage the hair.

Based on the study aimed at the solution of the aforementioned problems, the inventors arrived at the present invention. More specifically, it is an object of the present invention to provide a stable polyorganosiloxane emulsion composition that possesses excellent cosmetic functions required for dampness and smoothness. Another object is to provide a cosmetic raw material prepared from the aforementioned emulsion composition.

THE INVENTION

The above problems are solved by the present invention, which relates to a polyorganosiloxane emulsion composition comprising: (A) a polyorganosiloxane; (B) an N-acylalkyl taurine and/or a salt thereof, and (C) water, the content of cyclic organosiloxane oligomer in said component (A) being no more than 3.5 wt %. The invention also relates to a cosmetic raw material prepared from the aforementioned polyorganosiloxane emulsion composition.

The invention will be now described in more detail. A polyorganosiloxane (A) may normally have a linear, partially branched, or a branched structure. Silicon-bonded organic groups used in this compound may comprise substituted or non-substituted monovalent hydrocarbon groups such as methyl, ethyl, propyl, butyl, pentyl, hexyl, heptyl, octyl, decyl, dodecyl, or similar saturated aliphatic hydrocarbon groups; vinyl, allyl, hexenyl, or similar unsaturated aliphatic hydrocarbon groups; cyclopentyl, cyclohexyl, or similar saturated alicyclic hydrocarbon groups; phenyl, tolyl, naphthyl, or similar aromatic hydrocarbon groups, or aforementioned groups, in which hydrogen atoms bonded to their carbon atoms are partially substituted by halogen atoms or by organic groups such as epoxy, carboxyl, amino, methacrylic, or mercapto groups. The aforementioned polyorganosiloxane may also contain alkoxy groups or hydroxyl groups bonded to silicon atoms.

The following are examples of the aforementioned polyorganosiloxanes: α,ω-dihydroxypolydimethylsiloxane, α-hydroxy-ω-trimethylsiloxypolydimethylsiloxane, α,ω-dimethoxypolydimethylsiloxane, α-methoxy-ω-trimethylsiloxypolydimethyl-siloxane, α,ω-diethoxypolydimethylsiloxane, α-ethoxy-ω-trimethylsiloxy-polydimethylsiloxane, α,ω-di(trimethylsiloxy)polydimethylsiloxane, silanol-capped crosslinked polymethylsiloxane, methoxy-capped crosslinked polymethylsiloxane, ethoxy-capped crosslinked polymethylsiloxane, trimethylsiloxy-capped crosslinked polymethylsiloxane.

In these polyorganosiloxanes, some of the methyl groups may be substituted with ethyl groups, phenyl groups, vinyl groups, 3-aminopropyl groups, N-(2-aminoethyl)-3-aminopropyl groups, 3-methacryloxypropyl groups, 3-glycidoxypropyl groups or 3-carboxypropyl groups.

It should have a 25° C. viscosity within the range of from 100 to 100,000,000 mPa·s, preferably from 1,000 to 10,000,000 mPa·s, more preferably from 5,000 to 5,000,000 mPa·s, and even more preferably, from 100,000 to 5,000,000 mPa·s.

The content of the cyclic organosiloxane oligomer in component (A) should not exceed 3.5 wt. %, preferably less than 3.0 wt. %, more preferably, less than 2.5 wt. %, and even less than 2.0 wt. %.

The so-called cyclic organosiloxane oligomer of the present invention comprises a mixture of cyclic organosiloxanes (tetramer to octamer) having 4 to 8 silicon atoms. Among these, the cyclic organosiloxane tetramer should be contained in an amount less than 2.0 wt. %, preferably less than 1.5 wt. %, and more preferably, less than 1.0 wt. %.

The N-acylalkyl taurine and/or salt thereof (component (B)) are anionic surface-active agents used for emulsification and dispersion of component (A) in water. When a raw material is prepared from polyorganosiloxane that contains silanol groups, the aforementioned component (B) is used as a dehydration and polycondensation reaction catalyst.

Component (B) is represented by the following general formula: $R^3$—CO—$NR^4$—$C_2H_4$—$SO_3M$, where $R^3$ and $R^4$ are non-substituted monovalent hydrocarbon groups. The following are specific examples of these groups: methyl, ethyl, propyl, butyl, pentyl, hexyl, heptyl, octyl, decyl, dodecyl, myristyl, palmityl, stearyl, or a similar saturated aliphatic hydrocarbon groups; a vinyl, allyl, hexenyl, oleyl, or similar unsaturated aliphatic hydrocarbon groups; cyclopentyl, cyclohexyl, or similar saturated alicyclic hydrocarbon groups; phenyl, tolyl, naphthyl, or similar aromatic hydrocarbon groups. Here, $R^3$ and $R^4$ may be the same or different. It is recommended that $R^3$ contain 1 to 30 carbon atoms. It is also recommended that $R^4$ contain 1 to 6 carbon atoms. Among the aforementioned groups, methyl groups are more common.

In the above formula, M is selected from a hydrogen atom; a sodium, potassium or a similar alkali-metal atom; ammonium, or triethanol ammonium. The following are examples of compounds suitable for use as component (B): N-lauroylmethyl taurine sodium salt, N-myristoylmethyl taurine sodium salt, N-oleoylmethyl taurine sodium salt, N-stearoylmethyl taurine sodium salt, N-coconut fatty acid methyl taurine sodium salt, N-coconut fatty acid methyl taurine potassium salt, N-coconut fatty acid methyl taurine magnesium salt, N-palmitoylmethyl taurine sodium salt, N-stearoylmethyl taurine sodium salt, N-cetyloylmethyl taurine sodium salt, or the above compounds in not-yet neutralized state. The aforementioned compounds can be used individually or in combinations.

Among these, most preferable are N-acylalkyl taurine salts, especially sodium, potassium, ammonium, and triethanolamine salts favorable from the point of view of emulsification.

It is recommended that component (B) be used in an amount of 1 to 100 parts by weight, preferably 1 to 50 parts by weight, for each 100 parts by weight of component (A). If it is used in quantities beyond the recommended range, the emulsion will lose stability.

Component (C) is water, which is used as a medium for emulsification of component (A). Although there are no special limitations with regard to the amount in which water can be used, it is recommended to use it in an amount, which provides stable emulsion prior to and after emulsification. In general, however, water should be used within 30 to 1000 parts by weight for each 100 parts by weight of component (A).

A polyorganosiloxane emulsion composition of the present invention composed from aforementioned components (A) through (C) can be prepared by subjecting a polyorganosiloxane (a) with a molecular weight lower than that of component (A) to emulsification and polycondensation in water in the presence of an N-acylalkyl taurine and/or a salt thereof (component (B)). Component (a) may be represented by a polydiorganosiloxane having both molecular terminals capped with silanol groups and expressed by the following general formula (I): HO $(R^2_2SiO)_n$H, where $R^2$ are substituted or non-substituted monovalent hydrocarbons that can be the same or different.

The following are specific examples of such monovalent hydrocarbons: methyl, ethyl, propyl, butyl, pentyl, hexyl, heptyl, octyl, decyl, dodecyl, or similar saturated aliphatic hydrocarbon groups; vinyl, allyl, hexenyl, or similar unsaturated aliphatic hydrocarbon groups; cyclopentyl, cyclohexyl, or similar saturated alicyclic hydrocarbon groups; phenyl, tolyl, naphthyl, or similar aromatic hydrocarbon groups; n is a value at which the viscosity of the polyorganosiloxane is within the range of from 10 to 30,000 mPa·s at 25° C.

The aforementioned polyorganosiloxane can be exemplified by α,ω-dihydroxypolydimethylsiloxane (a), 1,3-dihydroxy-tetramethyldisiloxane, and 1,7-dihydroxy-octamethyltetrasiloxane.

Such silanol-capped polydiorganosiloxanes are normally synthesized by subjecting cyclic siloxane oligomers to ring-opening polymerization in the presence of an acidic catalyst such as sulfuric acid, or an alkaline catalyst such as potassium hydroxide or potassium silanolate, and by terminating the molecular chain with water.

Reaction products obtained by the aforementioned method normally contain non-reacted cyclic organosiloxane oligomers. According to the invention, it is recommended that the content of such oligomer does not exceed 2.5 wt. %, preferably does not exceed 1.5 wt. %, and even more preferably does not exceed 1.0 wt. %. It is also recommended that reaction product contain cyclic organosiloxane cyclic tetramers in an amount not exceeding 0.1 wt. %, preferably not exceeding 0.05 wt %, and even more preferably, not exceeding 0.01 wt. %.

The content of cyclic organosiloxane oligomers can be reduced, e.g., by removing residual cyclic organosiloxane oligomers from the polyorganosiloxanes obtained in a ring-opening polymerization by distillation in vacuum, e.g., by stripping or by treating in a thin-film evaporator.

During emulsification and polycondensation of the low-molecular-weight polyorganosiloxane (a) expressed by general formula (I), the reaction product can be additionally combined with hydrolyzable organosilane. In case the hydrolyzable organosilane has organic functional groups, such an addition can be used for introducing organic functional groups to the polyorganosiloxane of component (A).

The following are examples of the aforementioned hydrolyzable organosilanes: methyltrimethoxy silane, methyltriethoxysilane, tetraethoxysilane, 3-aminopropylmethyldiethoxysilane, 3-aminopropyltriethoxysilane, N-(2-aminoethyl)-3-aminopropyltriethoxysilane, N-(2-aminoethyl)-3-aminopropyltrimethoxysilane, N-(2-aminoethyl)-3-aminopropylmethyldiethoxysilane, N-(2-aminoethyl)-3-aminopropylmethyldimethoxysilane, 3chloropropyltriethoxysilane, 3-chloropropyl-trimethoxysilane, 3-chloropropylmethyldiethoxysilane, 3-chloropropylmethyl dimethoxysilane, 3-methacryloxypropyltriethoxysilane, 3-methacryloxypropyl-trimethoxysilane, 3-acryloxypropylmethyldiethoxysilane, 3-acryloxypropylmethyldimethoxysilane, 3-glycidoxypropyltriethoxysilane, 3-glycidoxypropyl-trimethoxysilane, 3-glycidoxypropylmethyldiethoxysilane, 3-glycidoxypropyl-methyldimethoxysilane, 3-mercaptopropylmethyldiethoxysilane, 3-mercaptopropyl-methyldimethoxysilane, 3-carboxypropylmethyldiethoxysilane, 3-carboxypropylmethyldimethoxysilane, p-vinylphenyltriethoxysilane, p-vinylphenyltri-methoxysilane, 2-(vinylphenyl)ethyltriethoxysilane, 2-(vinylphenyl)ethyl-trimethoxysilane, 3-(p-isopropenylbenzoylamino)propyltriethoxysilane, 3-(p-isopropenylbenzoylamino)propyltrimethoxysilane, N-methacryloyl-N-methyl-3-aminopropyltriethoxysilane, N-methacryloyl-N-methyl-3-aminopropyltrimethoxy-silane, N-lauroyl-N-methyl-3-aminopropylmethyldiethoxysilane, N-lauroyl-N-methyl-3-aminopropylmethyldimethoxysilane, N-acryloyl-N-methyl-3-aminopropyltriethoxysilane, N-acryloyl-N-methyl-3-aminopropyltrimethoxysilane, N-lauroyl-N-methyl-3-aminopropyltriethoxysilane, N-lauroyl-N-methyl-3-aminopropyltrimethoxysilane, N,N-bis (methacryloyl)-3-aminopropylmethyldiethoxysilane, N,N-bis (methacryloyl)-3-aminopropylmethyldimethoxysilane, N,N-bis (lauroyl)-3-aminopropyltriethoxysilane, and N,N-bis (lauroyl)-3-aminopropyltrimethoxysilane. These compounds can be used separately or in combinations of two or more.

The emulsion composition of the invention can be prepared, e.g., by premixing the silanol-capped polydiorganosiloxane (a) with water (C) and the lauroylmethyl taurine or its salts. The sequence of mixing may be arbitrary. For example, component (B) can be mixed with and dissolved in component (C) using a mixer with a stirrer, and while the components are in the stage of mixing, they can be combined with component (a). The mixture can then be emulsified in an emulsifier such as a homogenizer, colloidal mill, line mixer, sonolator, combination mixer, Turello mixer, homogenizer-mixer, or the like. In this procedure, after coarse emulsification in an emulsifier, such as a homogenizer, colloidal mill, or a line mixer, subsequent fine emulsification may be performed in a pressurized homogenizer or an ultrasonic homogenizer. If necessary, additional uniform emulsification and dispersion can then be conducted with an addition of water. Upon completion of emulsification, some amount of acid can be added. Addition of acid contributes to the formation in the reaction system of a lauroylmethyl taurine that acts as an emulsification and polymerization catalyst by replacing a part of sulfonic acid salts contained as an acidic constituent in the N-acylalkyl taurine with sulfonates.

In general, acids suitable for the aforementioned purpose are sulfuric acid, hydrochloric acid, phosphoric acid, or similar inorganic acids, or a formic acid, acetic acid, citric acid, or similar organic acids. Among these, sulfuric acid and hydrochloric acid are advantageous, as they themselves act as catalysts for a dehydration polycondensation reaction and accelerate the speed of polymerization even at low temperatures.

On the other hand, phosphoric, formic, acetic, and citric acids are advantageous from the point of view of restricting the amount of oligomers in the emulsion, since they retard development in the polycondensation reaction of such by-products as cyclic organosiloxane oligomers, even if those remain in the system.

There are no special limitations with regard to the amount of acid that can be added to the system, but in general the acid should be added in an amount of 0.05 to 10 parts by weight for each 100 parts by weight of component (A). Stirring is then continued, silanol groups of component (a) are subjected to polycondensation, and an emulsion of a high-molecular polyorganosiloxane is obtained. For increasing the rate of polymerization of polyorganosiloxane and for suppressing formation of by-products such as cyclic organosiloxane oligomers, it is recommended to conduct the polycondensation reaction at low temperatures. However, because excessive cooling adversely affects the stability of the emulsion, it is preferable to combine the ingredients and use an emulsion polymerization temperature of 0~25° C. or 0~15° C., which would be even more preferable.

Although the polymerization time varies depending on the amount of generated cyclic organosiloxane oligomers, preferably, it is within 48 hours, even more preferably, within 24 hours, and still more preferably, within 15 hours.

To suppress the content of oligomers after emulsion polymerization to within 3.5 wt %, it is necessary to bring polymerization to completion within a shorter period of time if the temperature is relatively high, and if the polymerization temperature is lower, then polymerization can be conducted for a longer time. After reaching the desired polymerization viscosity, component (B) and the acid are neutralized by adding an alkaline substance. Inorganic substances, such as sodium hydroxide, potassium hydroxide, ammonia, sodium carbonate, potassium carbonate, ammonium carbonate, potassium acetate; and amines, such as triethanolamine are suggested as examples of the alkaline substances.

Depending on the intended purpose, the viscosity may be controlled by using diorganopolysiloxanes having triorganosiloxy groups, such as trimethylsiloxy groups, as chain terminating agents.

Although there are no particular limitations on the concentration of polyorganosiloxane (A) in the emulsion of the present invention, preferably, the concentration should be 5~80 wt %, even more preferably, 25~75 wt %, and still more preferably, 30~65 wt %. This is due to the poor efficiency of emulsification if it is less than 5 wt % and to an increase in the viscosity of the emulsion and a deterioration of its working properties if it exceeds 80 wt %.

Nonionic surface active agents and anionic surface active agents other than component (B) can be added to the emulsion composition of the present invention in order to maintain its stability so long as this does not adversely affect the object of the present invention.

The anionic surface active agents are exemplified by sodium polyoxyethylene lauryl ether acetate, disodium polyoxyethylene lauryl sulfosuccinate, sodium polyoxyethylene lauryl ether sulfate, sodium α-olefinsulfonate, triethanolamine salt of dodecylbenzenesulfonic acid, and sodium polyoxyethylene lauryl ether phosphate.

The nonionic surface active agents are exemplified by glycerin monostearate, sorbitan monopalmitate, polyoxyethylene cetyl ether, polyoxyethylene lauryl ether, polyoxyethylene stearyl ether, polyoxyethylene stearate, polyoxyethylene sorbitan monolaurate, coconut fatty acid diethanolamide, polyoxyethyleneoxypropylene glycol, and modified silicone oil containing polyoxyethylene groups. Such surface active agents may be used either before or after emulsification.

In addition, antiseptics and bactericides can be added in order to prevent bacterial contamination, and pH-adjusting agents, mildew-proofing agents, rust preventives, etc. can be used as well.

Because the above-described polyorganosiloxane emulsion composition of the present invention uses N-acylalkyl taurine or its salts as the emulsifying agent and, in addition, the content of cyclic organosiloxane oligomers in the composition is kept within 3.5 wt %, the stability of the emulsion itself, silicone stability, as well as its compounding stability in various cosmetic products are excellent and it is characterized by a low irritation potential when applied to the skin and scalp and by extremely superior cosmetic performance in terms of moisture and smoothness.

Furthermore, it has the advantages of zero environmental contamination and high degree of safety for the human body.

Examples are provided regarding the cosmetic raw material of the present invention.

The cosmetic raw material of the present invention consists of the above-described polyorganosiloxane emulsion composition, and to further improve its compounding stability in cosmetics, other components known from the prior art as additives for cosmetic raw materials consisting of silicone emulsions can be added thereto so long as this does not adversely affect the purpose of the present invention.

Nonionic surface active agents, anionic surface active agents other than component (B), pH-adjusting agents, antiseptics, mildew-proofing agents, rust preventives, etc. are suggested as such additives. These components can be used singly or as a combination of several components.

There are no particular limitations on the order, in which these components are added, but it is preferable to add components that may slow down or impair emulsion polymerization, such as nonionic surface active agents, after the emulsion polymerization while strictly controlling the amount added.

Diethanolamine N-acyl-L-glutamate, triethanolamine N-acyl-L-glutamate, sodium N-acyl-L-glutamate, sodium alkanesulfonate, ammonium alkyl(12, 14, 16)sulfate, triethanolamine (1) alkyl(11, 13, 15)sulfate, triethanolamine (2) alkyl(11, 13, 15)sulfate, triethanolamine alkyl(12~14) sulfate, triethanolamine alkyl sulfate solution, sodium alkyl (12, 13)sulfate, sodium alkyl sulfate solution, sodium isethionate, sodium lactostearate, disodium undecylenoylamidoethyl sulfosuccinate, triethanolamine sulfooleate, sodium sulfooleate, disodium oleamido sulfosuccinate, potassium oleate, sodium oleate, morpholine oleate, oleyl sarcosine, oleylmethyl taurine sodium salt, potassium-containing soap base, potassium soap base solution, potassium soap, carboxylated polyoxyethylene tridodecyl ether, carboxylated polyoxyethylene tridodecyl ether sodium salt (3 E.O.), triethanolamine N-(hardened tallow fatty acid)-acyl-L-glutamate, sodium N-(hardened tallow fatty acid)-acyl-L-glutamate, sodium (hardened coconut oil fatty acid) glyceryl sulfate, sodium diundecylenoylamidoethyl sulfosuccinate, sodium sulfostearate, potassium stearate, triethanolamine stearate, sodium stearate, sodium N-stearoyl-L-glutamate, disodium stearoyl-L-glutamate, stearoylmethyl taurine sodium salt, dioctyl sodium sulfosuccinate, dioctyl sodium sulfosuccinate solution, disodium polyoxyethylene monooleylamido sulfosuccinate (2 E.O.) solution, disodium polyoxyethylene lauroyl ethanolamido sulfosuccinate (5 E.O.), disodium lauryl sulfosuccinate, diethanolamide cetylsulfate, sodium cetylsulfate, soap base, sodium cetostearyl sulfate, triethanolamine tridecyl sulfate, potassium palmitate, sodium palmitate, palmitoylmethyl taurine sodium salt, solution (30%) of sodium salt of castor oil fatty acid, ammonium polyoxyethylene alkyl ether sulfate (3 E.O.) solution, diethanolamine polyoxyethylene alkyl(12, 13) ether sulfate (3 E.O.) solution, triethanolamine polyoxyethylene alkyl ether sulfate (3 E.O.) solution, triethanolamine polyoxyethylene alkyl (11, 13, 15) ether sulfate (1 E.O.), triethanolamine polyoxyethylene alkyl (12, 13) ether sulfate (3 E.O.), sodium polyoxyethylene alkyl ether sulfate (3 E.O.) solution, sodium polyoxyethylene alkyl (11, 13, 15) ether sulfate (1 E.O.), sodium polyoxyethylene alkyl (11~15) ether sulfate (3 E.O.), sodium polyoxyethylene alkyl (12, 13) ether sulfate (3 E.O.), sodium polyoxyethylene alkyl (12~14) ether sulfate (3 E.O.), sodium polyoxyethylene alkyl (12~15) ether sulfate (3 E.O.), disodium polyoxyethylene alkyl (12~14) sulfosuccinate (7 E.O.), sodium polyoxyethylene undecyl ether sulfate, sodium polyoxyethylene octyl phenyl ether sulfate solution, ammonium polyoxyethylene oleyl ether sulfate, disodium lauryl polyoxyethylene sulfosuccinate, sodium polyoxyethylene nonyl phenyl ether sulfate, sodium polyoxyethylene pentadecyl ether sulfate, triethanolamine polyoxyethylene myristyl ether sulfate, sodium polyoxyethylene myristyl ether sulfate, sodium polyoxyethylene myristyl ether sulfate (3 E.O.), sodium polyoxyethylene lauryl ether acetate (16 E.O.) solution, ammonium polyoxyethylene lauryl ether sulfate (2 E.O.), triethanolamine polyoxyethylene lauryl ether sulfate, sodium polyoxyethylene lauryl ether sulfate, diethanolamine myristyl sulfate, sodium myristyl sulfate, potassium myristate, sodium N-myristoyl-L-glutamate, sodium myristoylmethylaminoacetate, myristoylmethyl-β-alanine sodium salt solution, myristoylmethyl taurine sodium salt, medicinal soap, magnesium-triethanolamine coco alkyl sulfate, triethanolamine N-cocoate acyl-L-glutamate, sodium N-cocoate acyl-L-glutamate, sodium coconut oil fatty acid ethyl ester sulfonate, potassium cocoate, potassium cocoate solution, sodium N-cocoate-tallowate acyl-L-glutamate, sarcosine cocoate, sarcosine triethanolamine cocoate, sarcosine sodium cocoate, triethanolamine cocoate, triethanolamine cocoate solution, sodium cocoate, sodium methyl alanine cocoate, sodium methyl alanine cocoate solution, potassium methyl taurine cocoate, sodium methyl taurine cocoate, sodium laurylaminodipropionate, sodium laurylaminodipropionate solution (30%), sodium lauryl sulfoacetate, sodium laurylbenzenesulfonate, laurylsulfuric acid, ammonium laurylsulfate, potassium laurylsulfate, diethanolamine laurylsulfate, triethanolamine laurylsulfate, sodium laurylsulfate, magnesium laurylsulfate, monoethanolamine laurylsulfate, potassium laurate, triethanolamine laurate, triethanolamine laurate solution, sodium laurate, triethanolamine laurate myristate, triethanolamine lauroyl-L-glutamate, sodium N-lauroyl-L-glutamate, lauroylsarcosine, lauroylsarcosine potassium salt, lauroyl sarcosine triethanolamine salt solution, lauroylsarcosine sodium salt, lauroylmethyl-β-alanine sodium salt solution, lauroylmethyl taurine sodium salt, and lauroylmethyl taurine sodium salt solution are suggested as specific examples of the anionic surface active agents.

Ethylene glycol fatty acid ethyls, polyethylene glycol fatty acid esters, propylene glycol fatty acid esters, polypropylene glycol fatty acid esters, glycol fatty acid esters, trimethylolpropane fatty acid esters, pentaerythritol fatty acid esters, glucoside derivatives, glycerin alkyl ether fatty acid esters, trimethylolpropane oxyethylene alkyl ethers, fatty acid amides, alkylolamides, alkylamine oxides, lanolin and its derivatives, castor oil derivatives, hardened castor oil derivatives, sterol and its derivatives, polyoxyethylene alkyl ethers, polyoxyethylene alkyl allyl ethers, polyoxyethylene alkylamines, polyoxyethylene fatty acid amides, polyoxyethylene alkylolamides, polyoxyethylene diethanolamine fatty acid esters, polyoxyethylene trimethylolpropane fatty acid esters, polyoxyethylene alkyl ether fatty acid esters, polyoxyethylene polyoxypropylene glycols, polyoxyethylene polyoxypropylene alkyl ethers, polyoxyethylene polyoxypropylene polyhydric alcohol ethers, glycerin fatty acid esters, polyglycerin fatty acid esters, polyoxyethylene glycerin fatty acid esters, sorbitan fatty acid esters, polyoxyethylene sorbitan fatty acid esters, and sucrose fatty acid esters, are suggested as specific examples of the nonionic surface active agents.

Hydrochloric acid, sulfuric acid, phosphoric acid, diammonium hydrogen phosphate, disodium hydrogenphosphate, dipotassium hydrogenphosphate, ammonium dihydrogenphosphate, sodium dihydrogenphosphate, potassium dihydrogenphosphate, trisodium phosphate, tripotassium phosphate, acetic acid, ammonium acetate, sodium acetate, potassium acetate, citric acid, sodium citrate, diammonium citrate, sodium carbonate, potassium carbonate, ammonium carbonate, sodium hydrogencarbonate, ammonium hydrogencarbonate, sodium hydroxide, potassium hydroxide, ammonia, and triethanolamine are suggested as specific examples of the pH-adjusting agents.

Benzoic acid, aluminum benzoate, sodium benzoate, isopropylmethylphenol, ethylhexanediol, lysozyme chloride, chlorhexidine hydrochloride, octylphenoxyethanol, orthophenylphenol, sodium perborate, photosensitive material No. 101, photosensitive material No. 201, photosensitive material No. 301, photosensitive material No. 401, chlorhexidine gluconate solution, cresol, chloramine T, chlorxylenol, chlorcresol, chlorphenesin, chlorohexidine, chlorobutanol, resorcin acetate, salicylic acid, sodium salicylate, domiphen bromide, zinc pyrithion, zinc pyrithion solution, sorbic acid, potassium sorbate, thianthol, thioxolone, thimol, chiram, dehydroacetic acid, sodium dehydroacetate, trichlorocarbanilide, trichlorohydroxydiphenyl ether, isobutyl paraoxybenzoate, isopropyl paraoxybenzoate, ethyl paraoxybenzoate, butyl paraoxybenzoate, propyl paraoxybenzoate, benzyl paraoxybenzoate, methyl paraoxybenzoate, sodium methyl paraoxybenzoate, parachlorophenol, sodium paraphenolsulfonate (dihydrate), halocarban, phenoxyethanol, phenol, hexachlorophane, mononitroguaiacol, mononitroguaiacol sodium, paradimethylaminostyrylheptylmethyllyazolinium iodide, lauryltrimethylammonium trichlorophenoxide, oxyquinoline sulfate, oxyquinoline phosphate, and resorcin are suggested as specific examples of the antiseptics, mildew-proofing agents, and rust preventives.

Adding and mixing the following various raw materials with the cosmetic raw material of the present invention allows for obtaining skin cosmetics that exhibit excellent compatibility with the skin and can impart it with superior moisture and smoothness.

The various raw materials that can be used in the skin cosmetics are exemplified by the above-described anionic surface active agents, nonionic surface active agents, pH-adjusting agents, antiseptics, mildew-proofing agents, rust preventives, etc., and, in addition to them, by avocado oil, almond oil, olive oil, cacao butter, sesame oil, wheat germ oil, safflower oil, shea butter, turtle oil, tung oil, persic oil, sunflower oil, grapeseed oil, macadamia nut oil, mink oil, egg yolk oil, Japan tallow, coconut oil, rosehip oil, hardened oil and other oils and fats; orange roughy oil, carnauba wax, candelilla wax, spermaceti wax, jojoba oil, montan wax, beeswax, lanolin and other waxes; liquid paraffin, Vaseline, paraffin, ceresin, microcrystalline wax, squalane, and other hydrocarbons; lauric acid, myristic acid, palmitic acid, stearic acid, oleic acid, behenic acid, undecylenic acid, oxystearic acid, linoleic acid, lanolic acid, synthetic fatty acids, and other higher fatty acids; ethyl alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldodecanol, isostearyl alcohol, and other alcohols; cholesterol, dihydrocholesterol, phytosterol, and other sterols; ethyl linoleate, isopropyl myristate, lanolin fatty acid isopropyl, hexyl laurate, myristyl myristate, cetyl myristate, octyldodecyl myristate, decyl oleate, octyldodecyl oleate, hexyldecyl dimethyloctanoate, cetyl isooctanoate, cetyl palmitate, glycerin trimyristate, glycerin tri(capryl-caprate), propylene glycol dioleate, glycerin triisostearate, glycerin triisooctanoate, cetyl lactate, myristyl lactate, diisostearyl malate, and other fatty acid esters; glycerin, propylene glycol, 1,3-butylene glycol, polyethylene glycol, sodium d,1-pyrrolidonecarboxylate, sodium lactate, sorbitol, sodium hyaluronate, and other humectants; cationic surface active agents; betaintype, amino acid-type, imidazoline-type, lecithin and other amphoteric surface active agents; iron oxides and other colored pigments, zinc oxide, titanium oxide, zirconium oxide, and other white pigments; mica, talc, sericite, and other skin-color pigments; dimethylpolysiloxane, methylphenylpolysiloxane, octamethylcyclotetrasiloxane, decamethylcyclopentasiloxane, polyether-modified silicone oil, amino-modified silicone oil, and other silicone oils; demineralized water; carrageenan, alginic acid, gum arabic, traganth, pectin, starch, xanthan gum, polyvinyl alcohol, polyvinyl pyrrolidone, sodium polyacrylate, polyethylene glycol, and other thickeners, silicone-acrylic copolymer, silicone resin, and acrylic polymers and other film-forming agents, and, furthermore, UV absorbers, anti-microbial agents, anti-inflammatory agents, antiperspirant agents, fragrance, anti-oxidants, and propellants. In addition, hand creams, skin creams, foundation, eye shadow, face wash, and body shampoo are specifically suggested as the skin cosmetics.

In addition, when the cosmetic raw material of the present invention is used in a hair-care cosmetic, in addition to the above-described anionic surface active agents, nonionic surface active agents, pH-adjusting agents and antiseptics, mildew-proofing agents, rust preventives, compounding it with various raw materials such as film-forming agents, anti-freezing agents, oily components, emulsifiers, wetting agents, anti-dandruff agents, anti-oxidants, chelating agents, UV absorbers, fragrances, and colorants makes it possible to obtain hair-care cosmetics that exhibit excellent adhesion to hair and are capable of imparting it with superior moisture and smoothness.

Specifically, the film-forming agents are exemplified by polymers of (meth)acrylic radical-polymerizable monomers and their copolymers with silicone compounds, poly(N-acylalkyleneimine), poly(N-methylpyrrolidone), silicone resins modified by fluorine-containing organic groups or amino groups, non-functional silicone resins. Although there are no particular limitations on the anti-freezing agents used, generally, we suggest ethanol, isopropyl alcohol, 1,3-butylene glycol, ethylene glycol, propylene glycol, and glycerin.

Materials typically used in cosmetics can be used as the oily components. Representatively suggested are microcrystalline wax, paraffin wax, spermaceti wax, beeswax, Japan wax, sugar cane wax, and other waxes or their mixtures, liquid paraffin, α-olefin oligomers, squalane, squalene, and other hydrocarbon oils or their mixtures, cetanol, stearyl alcohol, isostearyl alcohol, hardened castor oil-derived alcohol, behenyl alcohol, lanolin alcohol, and other linear or branched saturated or unsaturated unsubstituted or hydroxy-substituted higher alcohols or their mixtures, palmitic acid, myristic acid, oleic acid, stearic acid, hydroxystearic acid, isostearic acid, behenic acid, castor oil fatty acid, coconut oil fatty acid, tallow fatty acid, and other linear or branched saturated or unsaturated unsubstituted or hydroxy-substituted higher fatty acids or their mixtures, olive oil, coconut oil, rape seed oil, palm oil, palm kernel oil, castor oil, hardened castor oil, peanut oil, beef tallow, hydrogenated beef tallow, jojoba oil, hardened jojoba oil, monostearic acid glyceride, monooleic acid glyceride, dipalmitic acid glyceride, trimyristic acid glyceride, monooleic acid glyceride, oleyl oleate, isostearyl isostearate, palmityl behenate, isopropyl palmitate, stearyl acetate, dihydroxystearic acid ester, and other esters, linear, branched or cyclic low molecular silicone oils, amino-modified silicone oils, fatty acid-modified silicone oils, alcohol-modified silicone oils, polyether-modified silicone oils, phosphoric acid (phosphate)-containing silicone oils, fluorine-modified alkyl-containing silicone oils, alkyl-modified silicone oils, epoxy-modified silicone oils and other silicone oils, high molecular silicones, silicone resins soluble in solvents, liquid or crude rubber-like at room temperature or possessing thermoplastic properties or their mixtures.

The silicones are preferably latex-like, for example, one may suggest commonly used compounds, such as glycerin monostearate, sorbitan monopalmitate, polyoxyethylene cetyl ether, polyoxyethylene stearic acid ester and polyoxyethylene sorbitan laurate.

The wetting agents are exemplified by hexylene glycol, polyethylene glycol 600, sodium pyroglutamate, and glycerin.

The anti-dandruff agents are exemplified by sulfur, selenium sulfate, zinc pyridium-1-thiol-N-oxide, salicylic acid, 2,4,4'-trichloro-2'-hydroxydiphenyl ether, and 1-hydroxy-2-pyridone compounds.

BHA, BHT, and γ-oryzanol are suggested as the antioxidants.

The chelating agents are exemplified by ethylenediamine tetraacetate, citric acid, ethane-1-hydroxy-1,1-diphosphonic acid and their salts.

The UV absorbers are exemplified by benzophenone derivatives represented by 2-hydroxy-4-methoxybenzophenone, benzotriazole derivatives represented by 2-(2'-hydroxy-5'-methylphenyl)benzotriazole, cinnamic acid ester, etc.

Furthermore, other compounds suggested include, preferably, glycerin, propylene glycol, dipropylene glycol, 1,3-butylene glycol, and other polyhydric alcohols, monoalkyltrimethylammonium salts, dialkyldimethylammonium salts, and other quaternary ammonium salts, and, more specifically, stearyltrimethyl-ammonium chloride, behenyltrimethylammonium chloride, distearyldimethyl-ammonium chloride, dibehenyldimethylammonium chloride, and other cationic surface active agents, or amphoteric surfactants, squalane, lanolin, perfluoropolyether, cationic polymers, and other tactile sensation improvers, propylene glycol, glycerin, sorbitol and other humectants, methylcellulose, carboxyvinyl polymer, hydroxyethylcellulose, polyoxyethylene glycol distearate, ethanol, and other viscosity-adjusting agents, pearlescent agents, fragrances, pigments, dyes, propellants, vitamins, hair nourishing additives, hormones, and other medicinal agents, trichlosan, trichlorocarban and other antimicrobial agents, potassium glycyrrhizinate, tocopherol acetate, and other anti-inflammatory agents, zinc pirithion, octopyrox, and other anti-dandruff agents, methylparaben, butylparaben, and other antiseptics, propellants, and other components listed in the Encyclopedia of Shampoo Ingredients (Micelle Press, 1985).

In addition, specific examples of the hair-care cosmetics include shampoos, hair rinses, hair conditioners, hair treatment formulations, set lotions, blow styling aids, hair sprays, foam-type styling aids, gel-type styling aids, hair liquids, hair tonics, hair creams, hair growth aids, hair-nourishing aids, and hair dyes.

BEST MODE FOR CARRYING OUT THE INVENTION

EXAMPLES

The present invention is explained by referring to examples. In the examples, the words "part(s)" refers to "part(s) by weight," "%" stands for "wt %," and "cyclic organosiloxane oligomers" is a mixture of cyclic organosiloxane tetramer to cyclic organosiloxane octamer. The measurement of the physical properties and stability of the emulsion composition and hair/skin treatment were carried out using the following methods.

Content of Cyclic Organosiloxanes

Approximately 1 g of the emulsion was weighed and 10 ml hexane and 5 ml methanol were added thereto. The emulsion was broken down by energetic stirring, causing the organopolysiloxane to be sufficiently dissolved in the hexane layer. After allowing the mixture to stand in this state for 12~24 hours, 5 ml ion exchange water was added thereto, and the top hexane layer was subjected to gas chromatography measurements to determine the content of cyclic organosiloxane oligomers (D4~D8) and cyclic organosiloxane tetramer (D4).

Polyorganosiloxane Viscosity

After ensuring complete breakdown by adding acetone to the emulsion, oily components were removed therefrom. The oily components were washed with acetone, and then subjected to heat treatment for 15 minutes in an oven at 105° C., after which viscosity measurement was carried out at 25° C. using an E-type viscometer.

Stability

Fifty $cm^3$ of the obtained polyorganosiloxane emulsion was placed in a 100 $cm^3$ glass vial and the vial was tightly corked. The glass vial was placed for 30 days in an accelerated weathering tester set to repeat a 0-to-50° C. temperature cycle every 12 hours, and, upon passage of 30 days, changes in the external appearance and presence of oily components on the surface were evaluated. The results of the evaluation were represented in the following manner.

Changes in external appearance

◉: Uniform, no changes observed.
○: Some creaming observed at the top.
Δ: Creaming observed.
X: Separated into 2 layers.
- Oily components on the surface
○: Absolutely no oily components observed.
Δ: An insignificant amount of oily components observed.
X: Oily components observed over the entire surface.

Treatment of Hair

After pre-treatment of the hair to be treated, which was carried out by washing a bundle of hair weighing 5 g in 10 wt % aqueous solution of sodium polyoxyethylene (4) lauryl sulfate, the hair was rinsed with water and allowed to dry naturally over a period of 24 hours. The thus pre-treated hair was immersed in a hair-care shampoo composition for 10 seconds and thoroughly drained of excess liquid. After that, brushing was conducted until the hair was completely detangled, whereupon the hair was allowed to dry naturally for 24 hours. The thus shampoo treated hair was subjected to tactile evaluation by a panel of 30 people.

Treatment of Skin

The skin of 30 panelists was washed for 30 seconds using a body shampoo composition and thoroughly rinsed with running water. Tactile evaluation was carried out after completely removing moisture with a towel.

Synthesis Example 1

One thousand g of polydimethylsiloxane oil with both terminal ends of the molecular chain terminated by silanol groups (octamethylcyclotetrasiloxane content: 1.3%), which contained 5.4% cyclic dimethylsiloxane oligomers and had a viscosity of 65 mm$^2$/s, was placed in a 2000-mL round-bottomed flask and subjected to stripping for 12 hours in an evaporator with nitrogen bubbling at a reduced pressure of 10 mmHg and a temperature of 150° C., reducing the content of the cyclic dimethyl-siloxane oligomer to 0.4%. In addition, the content of octamethylcyclotetrasiloxane was determined to be 0.01%. Hereinbelow, the resultant polydimethylsiloxane oil is called "deoligomerized oil."

Example 1

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.35 microns. Subsequently, 0.5 parts of 36% hydrochloric acid was added to the emulsion, and the mixture was stored for 15 hours at a temperature of 5° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A-1). The physical properties and stability of the resultant emulsion composition were measured and the results were listed in Table 1.

Example 2

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.33 microns. Subsequently, 0.5 parts of 36% hydrochloric acid was added to the emulsion, and the mixture was stored for 24 hours at a temperature of 5° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A-2). The physical properties and stability of the resultant emulsion composition were measured and the results were listed in Table 1.

Example 3

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.36 microns. Subsequently, 0.5 parts of 36% hydrochloric acid was added to the emulsion, and the mixture was stored for 48 hours at a temperature of 5° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A-3). The physical properties and stability of the resultant emulsion composition were measured and the results were listed in Table 1.

Example 4

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.35 microns. Subsequently, 1.0 parts of 36% hydrochloric acid was added to the emulsion, and the mixture was stored for 48 hours at a temperature of 5° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A4). The physical properties and stability of the resultant emulsion composition were measured and the results were listed in Table 1.

Example 5

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.36 microns. Subsequently, 0.5 parts of 36% hydrochloric acid was added to the emulsion, and the mixture was stored for 15 hours at a temperature of 25° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A-5). The physical properties and stability of the resultant emulsion composition were measured and the results were listed in Table 1.

Example 6

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.34 microns. Subsequently, 0.5 parts of sulfuric acid was added to the emulsion, and the mixture was stored for 15 hours at a temperature of 25° C.

After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A-6). The physical properties and stability of the resultant emulsion composition were measured and the results were listed in Table 2.

Example 7

After dissolving 1.0 parts N-lauroylmethyl taurine sodium in 36.0 parts ion exchange water, 55.0 parts deoligomerized oil and 0.3 parts methyltrimethoxysilane were added to and pre-mixed with the solution. The mixed solution was passed twice through a homogenizer under a pressure of 350 kg/cm$^2$, obtaining a crude emulsion with an average particle size of 0.38 microns. Subsequently, 0.5 parts of 36% hydrochloric acid was added to the emulsion, and the mixture was stored for 20 hours at a temperature of 15° C. After that, stirring was continued and the polymerization reaction was terminated by dropwise addition of 5% aqueous solution of sodium carbonate until the pH was brought to approximately 7, obtaining a silanol-capped crosslinked polymethylsiloxane emulsion composition (A-7). The physical properties and stability of the resultant emulsion composition were measured and the results were listed in Table 2.

Example 8

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.38 microns. Subsequently, 0.5 parts of 36% hydrochloric acid was added to the emulsion, and the mixture was stored for 20 hours at a temperature of 15° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (A-8). The physical properties and stability of the resultant emulsion composition were measured and the results were listed in Table 2.

Comparative Example 1

After dissolving 1.0 parts dodecylbenzenesulfonic acid in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.33 microns. Subsequently, the mixture was placed in a separate container and stored for 15 hours at a temperature of 40° C. After that, stirring was continued and the polymerization reaction was terminated by dropwise addition of 5% aqueous solution of sodium carbonate until the pH was brought to approximately 7, obtaining an α,ω-dihydroxypolydimethylsiloxane emulsion composition (B-1). The physical properties and stability of the resultant emulsion composition were measured and the results were listed in Table 2.

Comparative Example 2

After dissolving 1.0 parts N-lauroylmethyl taurine sodium in 36.0 parts ion exchange water, 55.0 parts deoligomerized oil were added to and premixed with the solution. The mixed solution was passed twice through a homogenizer under a pressure of 350 kg/cm$^2$, obtaining a crude emulsion with an average particle size of 0.36 microns. Subsequently, 0.5 parts of 36% hydrochloric acid was added to the mixture and the mixture was stored for 48 hours at a temperature of 25° C. After that, stirring was continued and the polymerization reaction was terminated by dropwise addition of 5% aqueous solution of sodium carbonate until the pH was brought to approximately 7, obtaining a α,ω-dihydroxypolydimethylsiloxane emulsion composition (B-2). The physical properties and stability of the resultant emulsion composition were measured and the results were listed in Table 2.

Comparative Example 3

After dissolving 1.0 parts N-lauroylmethyl taurine sodium in 36.0 parts ion exchange water, 55.0 parts deoligomerized oil were added to and pre-mixed with the solution. The mixed solution was passed twice through a homogenizer under a pressure of 350 kg/cm$^2$, obtaining a crude emulsion with an average particle size of 0.35 microns. Subsequently, the mixture was placed in a separate container and stored for 15 hours at a temperature of 40° C. After that, stirring was continued and the polymerization reaction was terminated by dropwise addition of 5% aqueous solution of sodium carbonate until the pH was set to approximately 7, obtaining a α,ω-dihydroxypolydimethylsiloxane emulsion composition (B-3). The physical properties and stability of the resultant emulsion composition were measured and the results were listed in Table 2.

TABLE 1

|  | Ex. 1 | Ex. 2 | Ex. 3 | Ex. 4 | Ex. 5 |
| --- | --- | --- | --- | --- | --- |
| Sample No. | A-1 | A-2 | A-3 | A-4 | A-5 |
| N-lauroylmethyl taurine sodium | 1.0 | 1.0 | 1.0 | 1.0 | 1.0 |
| Dodecylbenzenesulfonic acid | — | — | — | — | — |
| Ion exchange water | 36.0 | 36.0 | 36.0 | 36.0 | 36.0 |
| Deoligomerized oil | 55.0 | 55.0 | 55.0 | 55.0 | 55.0 |
| Methyltrimethoxysilane | — | — | — | — | — |
| 36% hydrochloric acid | 0.5 | 0.5 | 0.5 | 1.0 | 0.5 |
| Sulfuric acid | — | — | — | — | — |
| 5% aqueous solution of | Appropriate | Appropriate | Appropriate | Appropriate | Appropriate |

TABLE 1-continued

|  | Ex. 1 | Ex. 2 | Ex. 3 | Ex. 4 | Ex. 5 |
|---|---|---|---|---|---|
| sodium carbonate | amount | amount | amount | amount | amount |
| Polymerization temperature (° C.) | 5 | 5 | 5 | 5 | 25 |
| Polymerization time (hours) | 15 | 24 | 48 | 48 | 15 |
| D4~D8 concentration* (%) | 1.3 | 1.8 | 2.7 | 2.4 | 2.7 |
| D4 concentration* (%) | 0.4 | 0.7 | 1.3 | 1.1 | 1.3 |
| Extract fluid viscosity (mPa.s) | 84,000 | 180,000 | 1,940,000 | 2,760,000 | 167,000 |
| Stability |  |  |  |  |  |
| Changes in external appearance | ◎ | ◎ | ◎ | ◎ | ◎ |
| Oily components on the surface | ○ | ○ | ○ | ○ | ○ |

*Concentration in silicone

TABLE 2

|  | Ex. 6 | Ex. 7 | Ex. 8 | Comp. Ex. 1 | Comp. Ex. 2 | Comp. Ex. 3 |
|---|---|---|---|---|---|---|
| Sample No. | A-6 | A-7 | A-8 | B-1 | B-2 | B-3 |
| N-lauroylmethyl taurine sodium | 1.0 | 1.0 | 1.0 | — | 1.0 | 1.0 |
| Dodecylbenzenesulfonic acid | — | — | — | 1.0 | — | — |
| Ion exchange water | 36.0 | 36.0 | 36.0 | 36.0 | 36.0 | 36.0 |
| Deoligomerized oil | 55.0 | 55.0 | 55.0 | 55.0 | 55.0 | 55.0 |
| Methyltrimethoxysilane | — | 0.3 | — | — | — | — |
| 36% hydrochloric acid | — | 0.5 | 0.5 | — | 0.5 | 0.5 |
| Sulfuric acid | 0.5 | — | — | — | — | — |
| 5% aqueous solution of sodium carbonate | Appropriate amount | Appropriate amount | Appropriate amount | Appropriate amount | Appropriate amount | Appropriate amount |
| Polymerization temperature (° C.) | 25 | 15 | 15 | 40 | 25 | 40 |
| Polymerization time (hours) | 15 | 20 | 20 | 15 | 48 | 15 |
| D4~D8 concentration* (%) | 1.9 | 2.8 | 2.7 | 4.9 | 7.2 | 5.3 |
| D4 concentration* (%) | 0.8 | 1.3 | 1.4 | 2.6 | 3.8 | 2.9 |
| Extract fluid viscosity (mPa.s) | 169,000 | Paste** 32,000,000 | 310,000 | 210,000 | 808,000 | 207,000 |
| Stability |  |  |  |  |  |  |
| Changes in external appearance | ◎ | ◎ | ◎ | ○ | ◎ | ◎ |
| Oily components on the surface | ○ | ○ | ○ | Δ | ○ | Δ |

*Concetration in silicone.
**Complex viscosity measured using dynamic analyzer ARES from Rheometric Scientific, Inc. used for measurement of viscoelastic properties.
Example 9

The polyorganosiloxane emulsion compositions A-1, A-2, A-3, A-4, A-7, and A-8 prepared in Examples 1~4 and Examples 7 and 8 were diluted with water so as to bring the concentration of polyorganosiloxane to 0.25%. A hair shampoo composition was prepared by combining 10 parts of the diluted emulsion with 90 parts of a hair shampoo base consisting of the components listed hereinbelow. Hair was treated with the resultant hair shampoo composition and subjected to tactile evaluation after treatment. In addition, its glossiness was observed with the naked eye. The results are listed in Table 3.

○ Hair shampoo base

| 25% aqueous solution of N-lauroylmethyl taurine sodium | 25.0 parts |
|---|---|
| Lauroyl sarcosine sodium | 6.0 parts |
| 25% aqueous solution of lauryldimethylbetain | 10.0 parts |
| Coconut fatty acid diethanolamide | 4.0 parts |
| Propylene glycol | 5.0 parts |
| Phenoxyethanol | 1.0 parts |
| o-[2-hydroxy-3-(trimethylammonio)propyl]hydroxyethylcellulose chloride | 0.5 parts |
| Ion exchange water | 38.5 parts |

Comparative Example 4

Using emulsion composition B-1 prepared in Comparative Example 1, a hair shampoo composition was prepared, hair treatment was conducted and its evaluation was carried out in the same manner as in Example 9. The results are listed in Table 3.

TABLE 3

| Sample No. | Example 9 | | | | | | Comp. Ex. 4 |
|---|---|---|---|---|---|---|---|
| | A-1 | A-2 | A-3 | A-4 | A-7 | A-8 | B-1 |
| Tactile evaluation (number of people among 30 panelists) | | | | | | | |
| Excellent tactile sensation | 28 | 29 | 30 | 30 | 30 | 30 | 24 |
| Somewhat inferior slipperiness | 2 | 1 | 0 | 0 | 0 | 0 | 1 |
| Inferior slipperiness | 0 | 0 | 0 | 0 | 0 | 0 | 5 |
| Subjective glossiness (number of people among 30 panelists) | | | | | | | |
| Glossy | 29 | 28 | 29 | 30 | 30 | 30 | 23 |
| Somewhat inferior glossiness | 1 | 2 | 1 | 0 | 0 | 0 | 2 |
| Inferior glossiness | 0 | 0 | 0 | 0 | 0 | 0 | 5 |
| Combined evaluation | Excellent | Excellent | Excellent | Extremely excellent | Extremely excellent | Extremely excellent | Unsatisfactory |

Example 10

The polyorganosiloxane emulsion compositions A-1, A-2, A-3, A-4, A-7, and A-8 prepared in Examples 1~4 and Examples 7 and 8 were diluted with water so as to bring the concentration of polyorganosiloxane to 1.0%. A body shampoo composition was prepared by combining 10 parts of the diluted emulsion with 90 parts of a body shampoo base consisting of the components listed hereinbelow. Skin was washed with the resultant body shampoo composition and subjected to tactile evaluation. The results are listed in Table 4.

○ Body shampoo base

| | |
|---|---|
| 30% aqueous solution of lauroyl sarcosine sodium | 15.0 parts |
| 27% aqueous solution of disodium lauryl sulfosuccinate | 15.0 parts |
| Ion exchange water | 60 parts |

Comparative Example 5

Using emulsion composition B-1 prepared in Comparative Example 1, a body shampoo composition was prepared and used to wash the skin, followed by evaluation in the same manner as in Example 10. The results are listed in Table 4.

TABLE 4

| Sample No. | Example 10 | | | | | | Comp. Ex. 5 |
|---|---|---|---|---|---|---|---|
| | A-1 | A-2 | A-3 | A-4 | A-7 | A-8 | B-1 |
| Tactile evaluation (number of people among 30 panelists) | | | | | | | |
| Excellent tactile sensation | 28 | 28 | 29 | 29 | 30 | 28 | 23 |
| Somewhat unsatisfactory tactile sensation | 2 | 2 | 1 | 1 | 0 | 2 | 2 |
| Unsatisfactory tactile sensation | 0 | 0 | 0 | 0 | 0 | 0 | 5 |
| Combined evaluation | Excellent | Excellent | Excellent | Excellent | Extremely excellent | Excellent | Unsatisfactory |

INDUSTRIAL APPLICABILITY

The emulsion composition of the present invention is useful as a silicone component added to raw materials for skin cosmetics and hair-care cosmetics. In other words, although not a cosmetic by itself, the emulsion composition is appropriate for use as a cosmetic raw material used in combination with other ingredients. The cosmetic material of the present invention is also characterized by abundant affinity to hair and skin and by a superior tactile sensation it provides.

What is claimed is:

1. A method of preparing a polyorganosiloxane emulsion composition including (A) 100 parts by weight of a polyorganosiloxane, (B) 1 to 100 parts of a material selected from the group consisting of (i) an N-acylalkyl taurine and (ii) a salt of N-acylalkyl taurine having the general formula:

$R^3$—CO—$NR^4$—$C_2H_4$—$SO_3M$, wherein $R^3$ and $R^4$ are non-substituted monovalent hydrocarbons, and M is selected from the group consisting of the hydrogen atom, an alkali metal, ammonium, and triethanol ammonium, and (C) 30 to 1000 parts of water, said method comprising the step of:
  subjecting (a) a polyorganosiloxane with a molecular weight lower than that of component (A) to emulsion and condensation polymerization in water in the presence of component (B).

2. The method as set forth in claim 1 further comprising the step of removing residual cyclic organolisoxane oligomers from component (A) to a content of cyclic organosiloxane oligomer in component (A) of 3.5 weight percent or less.

3. The method according to claim 1, wherein a content of cyclic organosiloxane oligomer in said component (a) is 2.5 weight percent or less.

4. The method according to claim 1, wherein a content of cyclic organosiloxane oligomer in said component (a) is 1.0 weight percent or less.

5. The method according to claim 1, wherein said component (B) is a compound expressed by the following general formula: $R^3$—CO—$NR^4$—$C_2H_4$—$SO_3M$ wherein $R^3$ and $R^4$ are non-substitute monovalent hydrocarbons, and M is selected from the group consisting of hydrogen atom, alkali metal atom, ammonium, and triethanol ammonium.

6. The method according to claim 1, wherein said component (B) is selected from the group consisting of N-lauroylmethyl taurine sodium salt, N-myristoymethyl taurine sodium salt, N-oleoymethyl taurine sodium salt, N-stearoylmethyl taurine salt, N-coconut fatty acid methyl taurine sodium salt, N-coconut fatty acid methyl taurine potassium salt, N-coconut fatty acid methyl taurine magnesium salt, N-palmitoylmethyl taurine sodium salt, N-stearoylmethyl taurine sodium salt, and N-cetyloymethyl taurine sodium salt.

7. The method according to claim 5, wherein said component (B) is selected from the group consisting of N-lauroylmethyl taurine sodium salt, N-myristoymethyl taurine sodium salt, N-oleoylmethyl taurine sodium salt, N-stearoylmethyl taurine sodium salt, N-coconut fatty acid methyl taurine sodium salt, N-coconut fatty acid methyl taurine potassium salt, N-coconut fatty acid methyl taurine magnesium salt, N-palmitoylmethyl taurine sodium salt, N-stearoylmethyl taurine sodium salt, and N-cetyloylmethyl taurine sodium salt.

8. The method according to claim 1, wherein a salt of an N-acylalky taurine is used as component (B), said salt being used in combination with an inorganic or organic acid.

9. The method according to claim 1, wherein a content of cyclic organosiloxane tetramer does not exceed 2.0 weight percent.

10. The method according to claim 1, wherein said component (A) is a polydimethylsiloxane.

11. The method according to claim 1, wherein the concentration of said component (A) in the emulsion is 5-80 weight percent.

12. The method as set forth in claim 1, wherein said component (a) is a polyorganosiloxane expressed by the following general formula (I):

HO $(R^2_2SiO)_nH$ where $R^2$ is selected from a group consisting of:
  (i) substituted monovalent hydrocarbons and
  (ii) non-substitute monovalent hydrocarbons, and wherein n has a value, at which the viscosity is within the range of 10 to 30,000 mPa-s at 25° C., and the viscosity of said component (A) is 100 to 100,000,000 mPa-s at 25° C.

13. The method according to claim 12, wherein a content of cyclic organosiloxane oligomer in said component (a) is 2.5 weight percent or less.

14. The method according to claim 12, wherein a content of cyclic organosiloxane oligomer in said component (a) is 1.0 weight percent or less.

15. The method according to claim 12, wherein said component (B) is a compound expressed by the following general formula: $R^3$—CO—$NR^4$—$C_2H_4$—$SO_3M$ wherein $R^3$ and $R^4$ are non-substitute monovalent hydrocarbons, and M is selected from the group consisting of hydrogen atom, alkali metal atom, ammonium, and triethanol ammonium.

16. The method according to claim 15, wherein said component (B) is selected from the group consisting of N-lauroylmethyl taurine sodium salt, N-myristoylmethyl taurine sodium salt, N-oleoylmethyl taurine sodium salt, N-stearoylmethyl taurine sodium salt, N-coconut fatty acid methyl taurine sodium salt, N-coconut fatty acid methyl taurine potassium salt, N-coconut fatty acid, methyl taurine magnesium salt, N-palmitoylmethyl taurine sodium salt, N-stearoylmethyl taurine sodium salt, and N-cetyloymethyl taurine sodium salt.

17. The method according to claim 12, wherein a salt of an N-acylalkyl taurine is used as component (B), said salt being used in combination with an inorganic or organic acid.

18. The method according to claim 12, wherein a content of cyclic organosiloxane tetramer does not exceed 2.0 weight percent.

19. The method according to claim 12, wherein the concentration of said component (A) in the emulsion is 5-80 weight percent.

20. A method of preparing a hair care cosmetic, the method comprising:
  (I) providing a hair care preparation;
  (II) preparing a cosmetic raw material consisting of a polyorganosiloxane emulsion composition including (A) 100 parts by weight of a polyorganosiloxane, (B) 1 to 100 parts of a material selected from the group consisting of (i) an N-acylalkyl taurine and (ii) a salt of N-acylalkyl taurine having the general formula:

$R^3$—CO—$NR^4$—$C_2H_4$—$SO_3M$, wherein $R^3$ and $R^4$ are non-substituted monovalent hydrocarbons, and M is selected from the group consisting of the hydrogen atom, an alkali metal, ammonium, and triethanol ammonium, and (C) 30 to 1000 parts of water, said method comprising the step of:
  subjecting (a) a polyorganosiloxane with a molecular weight lower than that of component (A) to emulsion and condensation polymerization in water in the presence of component (B); and
  (III) combining the hair care preparation with the cosmetic raw material to prepare a hair care cosmetic.

21. A method of preparing a skin care cosmetic, the method comprising:

(I) providing a skin care preparation;
(II) preparing a cosmetic raw material consisting of a polyorganosiloxane emulsion composition including (A) 100 parts by weight of a polyorganosiloxane, (B) 1 to 100 parts of a material selected from the group consisting of (i) an N-acylalkyl taurine and (ii) a salt of N-acylalkyl taurine having the general formula:

$$R^3\text{—CO—}NR^4\text{—}C_2H_4\text{—}SO_3M,$$

wherein $R^3$ and $R^4$ are non-substituted monovalent hydrocarbons, and M is selected from the group consisting of the hydrogen atom, an alkali metal, ammonium, and triethanol ammonium, and (C) 30 to 1000 parts of water, said method comprising the step of:

subjecting (a) a polyorganosiloxane with a molecular weight lower than that of component (A) to emulsion and condensation polymerization in water in the presence of component (B); and (III) combining the skin care preparation with the cosmetic raw material to prepare a skin care cosmetic.

* * * * *

UNITED STATES PATENT AND TRADEMARK OFFICE
CERTIFICATE OF CORRECTION

PATENT NO.       : 7,300,648 B2
APPLICATION NO.  : 10/475377
DATED            : November 27, 2007
INVENTOR(S)      : Tadashi Hamachi et al.

Page 1 of 1

It is certified that error appears in the above-identified patent and that said Letters Patent is hereby corrected as shown below:

On the Title Page
In Section (73) Assignee: delete [Dowecorning] and insert therein --Dow Corning--

Column 21, line 19, after cyclic delete [organolisoxane], and insert therein --organosiloxane--

Column 22, line 31, delete the [,] between the words "acid" and "methyl"

Signed and Sealed this

Fifth Day of August, 2008

JON W. DUDAS
*Director of the United States Patent and Trademark Office*